United States Patent [19]
Klein et al.

[11] Patent Number: 6,134,011
[45] Date of Patent: Oct. 17, 2000

[54] OPTICAL MEASUREMENT SYSTEM USING POLARIZED LIGHT

[75] Inventors: David L. Klein; Gerard H. Vurens, both of Palo Alto, Calif.

[73] Assignee: HDI Instrumentation, Santa Clara, Calif.

[21] Appl. No.: 09/153,646

[22] Filed: Sep. 15, 1998

Related U.S. Application Data

[63] Continuation-in-part of application No. 09/090,434, Jun. 4, 1998, abandoned.
[60] Provisional application No. 60/059,498, Sep. 22, 1997.

[51] Int. Cl.[7] .................................................. G01J 4/04
[52] U.S. Cl. ...................... 356/369; 356/237.2; 356/381; 250/225
[58] Field of Search .................................. 356/364–369, 356/381, 382, 236; 250/225

[56] References Cited

U.S. PATENT DOCUMENTS

| | | | |
|---|---|---|---|
| 3,904,293 | 9/1975 | Gee | 356/369 |
| 4,585,348 | 4/1986 | Chastang et al. | 356/369 |
| 4,681,450 | 7/1987 | Azzam | 356/367 |
| 4,872,758 | 10/1989 | Miyazaki et al. | 356/381 |
| 4,893,932 | 1/1990 | Knollenberg | 356/369 |
| 4,908,508 | 3/1990 | Dubbeldam | 250/225 |
| 5,102,222 | 4/1992 | Berger et al. | 356/367 |
| 5,311,285 | 5/1994 | Oshige et al. | 356/369 |
| 5,335,066 | 8/1994 | Yamada et al. | 356/364 |
| 5,438,415 | 8/1995 | Kazama et al. | 356/369 |
| 5,644,562 | 7/1997 | De Groot | 356/369 |
| 5,726,455 | 3/1998 | Vurens | 356/369 |
| 5,790,259 | 8/1998 | Mizuhata et al. | 356/445 |
| 5,835,220 | 11/1998 | Kazama et al. | 356/237 |

OTHER PUBLICATIONS

Azzam, R.M.A. "Ellipsometry" *Handbook of Optics: Devices, Measurements & Properties* vol. II, 2nd edition, Bass, M. et al. (eds), McGraw–Hill, Inc.: chapter 27, pp. 27.1–27.26 (1995).

Herman, I.P. *Optical Diagnostics for Thin Film Processing*, Academic Press, Inc., San Diego, California: chapter 9.11.2, pp. 435–442 (1996).

Jellison, Gerald E. et al. "Two–channel Polarization Modulation Ellipsometer" *Applied Optics* 29(7):959–974 (1990).

*Primary Examiner*—Hoa Q. Pham
*Attorney, Agent, or Firm*—Lahive & Cockfield, LLP

[57] ABSTRACT

An optical measurement system for evaluating the surface of a substrate or the thickness and optical characteristics of a thin film layer overlying the substrate includes an intensity stabilized light source configured to generate a stabilized light beam, a polarizing element for polarizing the light beam emanating from the light source, and a detection system for measuring the light reflected from the substrate The measurement system includes a polarizing beam-splitter for splitting the light reflected from the substrate into s-polarized light and p-polarized light. The measurement system further includes two optical sensors for separately measuring the amplitude of the s-polarized light and the intensity of the p-polarized light and a third detector for measuring either the phase difference between the s-polarized light and the p-polarized light or the reflection angle of the light reflected from the substrate. A control system analyzes the measured amplitude of the s-polarized light and the p-polarized and either the phase-difference or the reflection angle to determine changes in the topography of substrate or changes in the thickness or optical characteristics of the thin film layer.

15 Claims, 3 Drawing Sheets

6,134,011

OPTICAL MEASUREMENT SYSTEM USING POLARIZED LIGHT

REFERENCE TO RELATED APPLICATIONS

This application is a continuation-in-part of copending U.S. patent application Ser. No. 09/090,434, filed Jun. 4, 1998, now abandoned which claims the benefit of U.S. Provisional Application No. 60/059,498, filed on Sep. 22, 1997. Both of the above-referenced patent applications are incorporated herein by reference.

BACKGROUND OF THE INVENTION

The present invention relates to measurements of partially light-transmissive thin films or layers of such films, and to measurements of surface topography or detection of surface defects. It specifically relates to optical measurement or detection, and to apparatuses for performing such optical measurement or detection of a thin film or a substrate surface.

A number of common articles of manufacture now have constructions involving thin films formed on relatively large area smooth substrates, and substrates wherein the underlying surface is reflective, possibly conductive, and at least visually smooth if not optically flat. To develop manufacturing processes for reliably fabricating these articles and to inspect them or understand the defects which arise in these articles, it is necessary to observe the thin films and the underlying substrate. These films may be liquid or solid, have a thickness substantially under one wavelength of the observation illumination, and may possess features or defects which are observable only with meticulous methodology against the highly reflective substrate, requiring a special instrument. To detect changes occurring on such a thin surface coating is an even more challenging task.

Various optical diagnostic methods, such as reflection ellipsometry, have been proposed to study thin film layers and surfaces. Reflection ellipsometry is the measurement of the change in polarization of light upon reflection from a specular surface to obtain information about the surface. Conventional automatic ellipsometers employ a rotating optical element, usually a rotating analyzer, to measure the polarization of the specularly reflected light beam. A significant drawback of these ellipsometers is that the instruments are relatively slow and thus are not suitable for real-time analysis.

A somewhat faster ellipsometer, a polarization-modulated ellipsometer (PME), is described in a paper of Jellison and Modine (*Applied Optics*, Vol. 29, No. 7, pg. 959 (March 1990)). This ellipsometer employs a photo-elastic modulator that dynamically elliptically polarizes the light incident on the sample surface and separates the analyzed light into orthogonally polarized beams using a Wollaston prism. The time resolution of this system is limited by the modulation frequency of the phase modulator which is approximately 50 kHz. The optimal time resolution of this type of ellipsometer is described as 10-ms, which remains impractical for real-time or in-situ analysis during processing or, in the case of magnetic storage disks, during use.

As the above described and other prior art devices and methods for performing optical measurement or detection of a thin film or a substrate surface have proven less than optimal, it is an object of the present invention to provide nondestructive diagnostic systems and methods having improved sensitivity, speed, and time resolution.

Another object of the present invention is to provide optical measurement systems and methods in which the surface of a substrate can be analyzed by a single optical scan of the substrate surface.

A further object of the present invention is to provide optical measurement systems and methods for real-time and in situ measurement and detection of changes or defects in a thin film layer and the underlying substrate surface.

Other general and more specific objects of this invention will in part be obvious and will in part be evident from the drawings and the description which follow.

SUMMARY OF THE INVENTION

The present invention is directed to an optical measurement system for evaluating the surface of a substrate or the thickness and optical characteristics of a thin film layer overlying the substrate. The optical measurement system of the present invention provides for the measurement of at least three parameters simultaneously, thereby increasing the speed and time resolution of the system by requiring only a single scan of the substrate to analyze the substrate, while concomitantly increasing the sensitivity of the system to changes in the substrate surface or to changes in the thickness and optical characteristics of the thin film layer overlying the substrate. The measured parameters include the amplitude of the s-polarized and the p-polarized light components received from the substrate, as well as at least a third parameter, which can be, for example, the phase difference between the s-polarized and the p-polarized light components, the reflection angle of the light beam reflected from the substrate surface, or the amplitude of scattered light reflected from the substrate. Additionally, the present invention contemplates the simultaneous measurement of additional parameters, including all of the above-referenced parameters, as well as the simultaneous measurement of alternate combinations of these parameters.

According to one embodiment of the present invention, the optical measurement system includes an intensity stabilized light source configured to generate a stabilized light beam, a polarizing element for polarizing the light beam emanating from the light source, and a detection system for measuring the light after interaction with the substrate. The detection system includes a polarization analyzing element for splitting the light after interaction with the substrate into s-polarized light and p-polarized light. The polarization analyzing element can be, for example, a polarizing beam splitter. The measurement system further includes two optical sensors for separately measuring the amplitude of the s-polarized light and the amplitude of the p-polarized light and a third optical sensor for measuring the phase difference between the s-polarized light and the p-polarized light. A control system is configured to analyze the measured amplitude of the s- and the p-polarized light and the phase difference to determine changes in the topography of substrate or changes in the thickness or optical characteristics of the thin film layer.

According to an alternative embodiment of the present invention, the optical measurement system includes an intensity stabilized light source configured to generate a stabilized light beam, a polarizing element for polarizing the light beam emanating from the light source, and a detection system for measuring the light reflected from the substrate. The detection system includes a polarization analyzing elements for splitting the light after interaction with the substrate into s-polarized light and p-polarized light. The polarization analyzing element can be, for example, a polarizing beam splitter. The measurement system further includes two optical sensors for separately measuring the amplitude of the s-polarized light and the amplitude of the p-polarized light and a third optical sensor for measuring the reflection angle of the light reflected from the substrate. A control system is configured to analyze the measured amplitude of the s-polarized light and the p-polarized and the reflection angle to determine changes in the topography of substrate or changes in the thickness or optical characteristics of the thin film layer.

In an alternative embodiment of the invention, the optical measurement system can include a system for collecting and measuring scattered light reflected from the substrate surface to obtain information concerning the roughness of the substrate surface. The system for collecting and measuring scattered light can include an integrating sphere for collecting the scattered light and a photo-diode for measuring the intensity of the scattered light.

In one embodiment, the system includes a light source feedback system for controlling and stabilizing the light beam from the light source. The light source feedback system can include a photo-diode for measuring the intensity of the light beam and a light source controller for controlling and stabilizing the light beam based on the measured intensity. A non-polarizing beam splitter can be used to direct a portion of the light beam from the light source to the photo-diode for measurement. The light source feedback system can be integrated into the light source or, in the alternative, can be a separate, stand-alone sub-system of the illumination system of the optical measurement system of the present invention. Alternatively, the light source feedback system can be used solely to monitor the light beam from the light source for use in calculations, without control or stabilization of the light beam.

The optical system of the present invention preferably includes a controllable translatable assembly for moving the polarized light beam across a portion of the substrate. A position indicator can be employed to determine the particular locations on the substrate upon which the polarized light beam impinges. Preferably, the control systems compiles a data set, an image intensity map, correlating the measured amplitude of the s-polar light, p-polar light, and scatter light, as well as the phase difference and the reflection angle, with the particular location on the substrate upon which the light source impinges. The image intensity map can be stored in a memory storage device provided with the control system.

BRIEF DESCRIPTION OF THE DRAWINGS

These and other features and advantages of the present invention will be more fully understood by reference to the following detailed description in conjunction with the attached drawings in which like reference numerals refer to like elements and in which.

DETAILED DESCRIPTION

Figure 1:
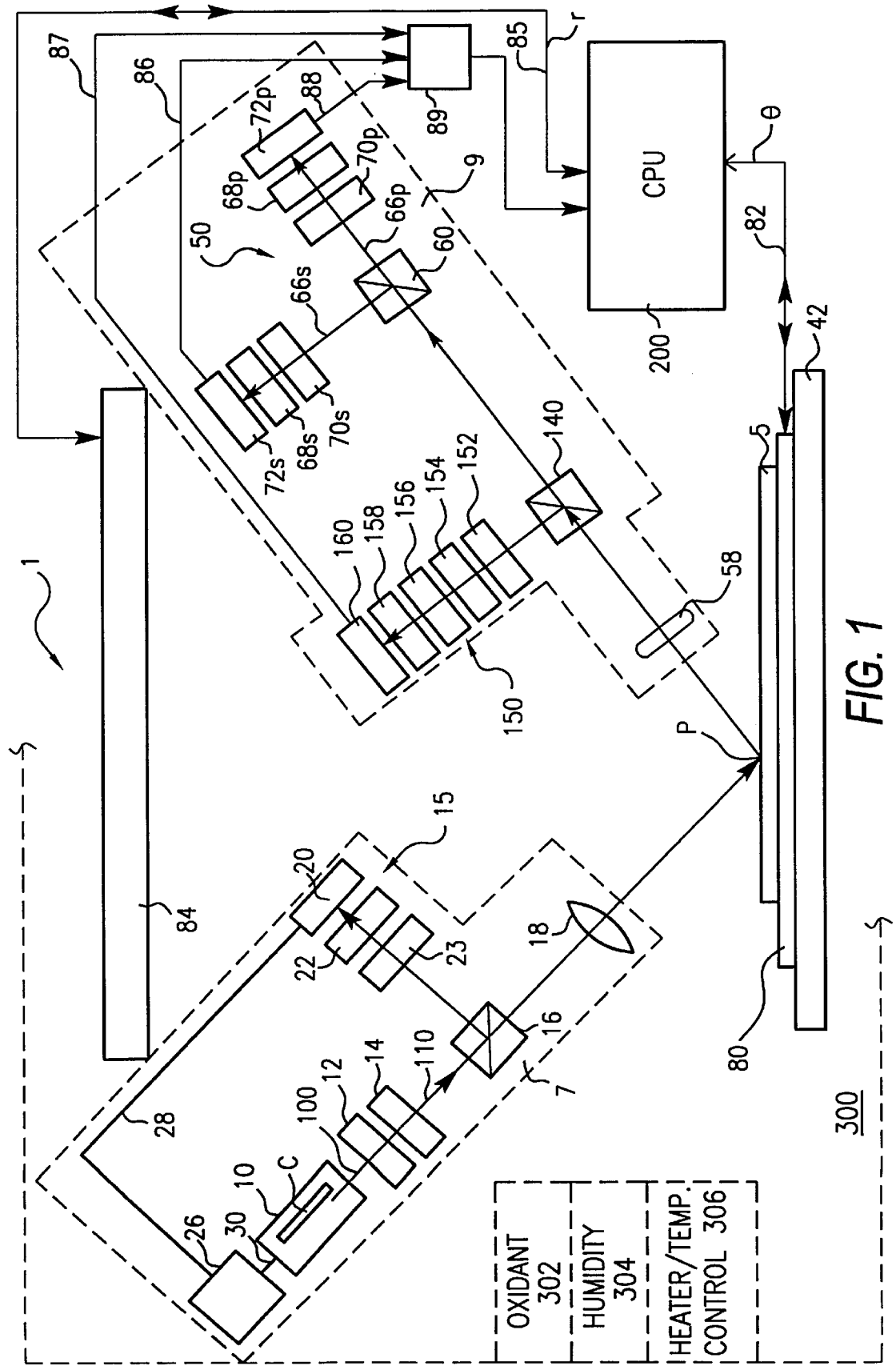
FIG. 1 is a schematic side view showing an optical measurement system in accordance with a first embodiment of the present invention.

An optical measurement system 1 for evaluating the topography of a substrate 5 and the thickness or optical characteristics of thin film layer overlying the substrate 5 in accordance with a first embodiment of the present invention is shown in FIG. 1. The components of the optical measurement system 1 include illumination system 7 for producing a polarized light beam and a detection system 9 for measuring the intensity and the phase difference of the components of the polarized light reflected from the substrate.

The substrate 5 to be tested is supported by a test stand or base 42 and the illumination system 7 and the detection system 9 are movably suspended on a track or stage 84 for one-dimensional translational movement along an axis perpendicular to the plane of the paper as shown in FIG. 1 over the base 42. Base 42 includes a motor driven turntable 80, e.g., a conventional so-called hard disk drive for rotating the substrate 5, for example a magnetic media storage disk, as well as a magnetic head and carrier of conventional type (not shown) for tribological testing of the disk as well as for reading information from and writing information onto the disk. Turntable 80 turns on a shaft (not shown) which has a 512 position shaft encoder, and corresponding angular position signals corresponding to a shaft rotation angle $s_\theta$ appear on line 82, which connects via appropriate circuitry to synchronize measurement acquisition in a processor, CPU 200. The position signals include a zero-position synchronization or framing signal, followed by the 215 encoder signals, after suitable signal conditioning, in each rotation. The turntable may, for example, turn at 3,600 or 5,400 RPM, corresponding to thirty or forty-five thousand shaft encoder positions per second; if measurement speed is critical, a faster motor, for example, 7,200 RPM or 10,000 RPM, a more finely divided shaft encoder, and/or special control chips may be used to interpolate sample positions or otherwise increase the number of data points per second.

Above the turntable 80, the movable illumination system 7 and the detection system 9 are mounted so that they are positioned and aligned symmetrically about a probe a point P in the plane of disk 5. Movement of the assembly stage 84 scans the point P radially across the disk. Stage 84 is stepper controlled in one micrometer or less increments, and position indicating and control signals are continuously monitored or controlled by CPU 200 on line 85, to synchronize or coordinate the r, θ positions illuminated on the substrate 5 with optical results from the illumination system 7 and the detection system 9 which are provided to CPU 200, after suitable conditioning by A/D converter 89, along lines 86, 87, and 88.

In the alternative, the turntable 80 or the base 42 can be mounted on a translatable table (not shown) to effect scanning of the point P across the surface of the substrate 5 as the turntable 80 rotates. In this arrangement, a separate stepper for stage 84 would be unnecessary.

The illumination system 7 can include a light source 10 which emits an intensity stabilized linearly polarized light beam 100. The light source 10 can be a laser source such as a four milliwatt laser diode producing a stable 670 nm output beam. The polarization quality of the light beam 100 can be improved by adding a linear polarizer 12 in the optical path after the light source 10. The light beam 100 is preferably circularly polarized by a zero-order quarter wave plate 14 having an optic axis offset 45° from the optic axis of the polarizer 12. In the alternative, light beam 100 can be linearly polarized at 45° by rotating the light source 10 and the polarizer 12 by 45° about the optic axis and by eliminating the quarter wave plate 14. Additionally, the light beam 100 can be elliptically polarized, however, circular polarized light and 45° linear polarized light are preferred.

The polarized light 110 is focused to a small spot on the substrate 5 by objective 18. The objective 18 is can be a simple but high quality, e.g. diffraction limited, focusing assembly such as Melles Griot 06 GLC005, with a focal length of 48 mm. This produces approximately a 7 micron spot size from the laser diode output at the surface of the disk.

Within the light source 10 a temperature sensor, which is integral with or contiguous to the laser diode, is used to develop control signals for a solid state Peltier effect cooler C that is energized to maintain the laser cavity of the laser diode at a fixed temperature. This prevents the laser output from jumping between cavity modes as the laser operates.

The laser is preferably also operated at a constant output or intensity stabilized level. Such output control may be achieved in several ways. For example, an external light source feedback system 15 can provide a fixed portion of the output beam energy to photo-detector 20 to develop a laser amplitude signal, which is fed in a negative feedback loop to a laser current drive, light source controller 26, thus producing a constant amplitude laser output. An optical diffuser 22 and a bandpass filter 23 can also be provided to reduce the possibility of stray light influencing the measurement of light source intensity at the photo-diode 20 and ensure the uniformity of the light reaching the photo-diode 20. The light source controller 26 receives the output signal from the photo-diode 20 along line 28 and controls the output of the light source along line 30 to effect intensity stabilization of light source 10. The light source controller 26 can be integrated into the light source 10. The beam splitter 16 may be formed integrally with the laser diode (such as by providing a partially transmissive, e.g., 0.01% transmissive, back face of the diode cavity). In addition, the light source controller 26 can be part of a separate external feedback control system, as illustrated in FIG. 1, or can be integrated into central CPU 200.

Moreover, the light source feedback system 15 can be used solely to monitor or measure the intensity of the light source 10. In this configuration, the intensity measurements from the light source feedback system can be monitored and later analyzed by CPU 200. For example, light source intensity fluctuations occurring during a measurement procedure can be compensated for during analysis by the CPU 200 using the measured intensity provided by the feedback system 15.

The detection system 9 is mounted on the same stage or carriage as the illumination system 7 and is positioned at an equal angle of incidence over the substrate to receive the light beam reflected from the point P on the substrate. The detection system 9 includes a collimator 58 and a non-polarizing beam splitter 140 that splits the reflected light beam into two identical components for measurement by two detection sub-systems, a phase detection subsystem 150 and an intensity detection subsystem 50.

The phase detection subsystem includes a color filter 152 and a quarter wave plate 154 and a linear polarizer 156 which operate to analyze the degree to which the reflected light beam received from the beam splitter 140 is circularly polarized. The linear polarizer 156 is rotated 45° relative to the quarter wave plate 154. The circularly polarized reflected light beam is received by a photo detector 160 which measures the phase difference between the two orthogonally polarized components, i.e., the s-polarized component and the p-polarized component, of the reflected light beam. A diffuser 158 can be provided to inhibit the effect of substrate flatness on the measurement. It is also possible to omit the quarter wave plate 154 and use a 45° orientation for the polarizer 156.

The intensity detection subsystem 50 includes a polarizing beam splitter 60 which splits light reflected from the substrate 5 into two linear polarized light beam components, an s-polarized light beam 66s and a p-polarized light beam 66p. The detection system 9 includes two photo-diodes 72s and 72p for separately measuring the intensity of the s-polarized light beam 66s and the p-polarized light beam 66p, respectively. Thus, the photo-diodes 72s and 72p at each point in time produce an output indicative of the intensity of both the s-polarized light and the p-polarized light reflected from point P. Optical diffusers 68s and 68p and bandpass filters 70s and 70p can also be provided to reduce the possibility of stray light influencing laser intensity and ensure light uniformity. The optical diffusers 68s and 68p can each be replaced with an integrating sphere to decrease sensitivity to beam angle variations.

The substrate to be evaluated can be, for example, a magnetic storage disk of a standard commercial size, e.g., about sixty-five or ninety-five millimeters in diameter, and by way of example, may be formed of glass or of an aluminum/magnesium material about 0.8 mm thick. On the surface of a representative disk substrate is deposited a 10–15 micrometer thick nickel-phosphorous layer, followed by a layer of chromium about one thousand Angstroms thick. The actual magnetic storage layer is then laid down as a 500 Angstrom thick layer of a cobalt/platinum/chrome magnetic alloy medium. These layers form a totally reflective top of the disk. A planarizing layer of carbon about 150 Angstroms thick is then deposited over the magnetic storage layer, and a layer of lubricant, such as a perfluoropolyether with a thickness of about twenty Angstroms, is applied over the carbon layer.

A representative cycle of operation of the optical measurement system 1 proceeds as follows. The illumination system 7 provides a circularly or 45° linearly polarized light beam 110, having both s-polarization components and p-polarization components, at a constant wavelength and a constant intensity level monitored by the light source feedback system 15. As the turntable 80 rotates, the polarized light beam 110 is moved radially to step through the radial extent of the disk, and the CPU 200 stores digitized representations of the collected beam power and the phase difference for each point specified by coordinates (r, θ) on the disk, as measured by the detection system 9. This data collection provides a quantitative record or map of reflectance of all points on the substrate for the both s- and p-polarization states, as well as the phase difference between the s- and p-polarization states.

The optical measurement system 1 can be operated within a closed environmental test chamber 300, provided with heaters and temperature control system 306, together with suitable means for forming or connecting to sources 302, 304 of humidity, oxidant or other environmental agents which may be selectively actuated to expose the substrate surface to a variety of environmental test conditions. During such exposure, normal processing operations are carried out on the substrate to measure changes in the substrate surface. For example, in the case of a magnetic storage disk, a magnetic head is carried across the face of the disk over the lubricant layer, so various effects such as frictional wear, lubricant erosion or redistribution, and the like occur.

In a further representative protocol, following operation under the test conditions, a second set of reflectance measurements are made to compile a second map, or a comparative reflectance map, of the same substrate. During all this time, the substrate preferably remains on the turntable so that there is an exact correspondence between the points with fixed (r,θ) coordinate in each data set stored by the CPU 200.

Thus, if surface reflectance maps are made with s- and p-polarizations both before and after testing, one has available information on both the changes in s- and p-polarization reflectance and changes in the phase difference between the s- and p-polarizations, and the relative amounts of s- and p-polarization reflection at each time.

The optical system 1 of the present invention provides significant advantages over conventional optical measurement systems by permitting simultaneous measurement of at least three parameters: 1) the intensity of the s-polarized light component reflected from the substrate; 2) the intensity of the p-polarized light reflected from the substrate surface (collectively, the s- and p-polarization reflectance); and 3) the phase difference between the s- and p-polarization components reflected from the substrate. In this manner, separate scans for each parameter across the surface of the substrate are not necessary. This significantly increases the data acquisition rate of the present system when compared with prior art polarizing systems, such as the apparatus disclosed in the copending U.S. application by the same inventor, Ser. No. 08/640,567, incorporated herein by reference, while concomitantly increasing the sensitivity of the system to the changes in the substrate by providing additional information about the substrate in the form of an additional measurement parameter. The optical instrument of the present invention, thus, affords the flexibility and adaptability to be configured to perform accurate, real time, in situ measurements of the substrate under operation conditions or during production.

Measurement of the three parameters permits the calculation of three ellipsometric parameters: the amplitude ratio $\Psi$, defined as the amplitude ratio of the p-polarization component to s-polarization component of the light reflected from the substrate surface, the phase difference $\Delta$, defined as the difference in phase between the p-polarization component and the s-polarization component, and the total reflectivity r. The these ellipsometric parameters can be calculated from the following equations:

$$\psi = \tan^{-1}(R_p/R_s)^{1/2} \quad (1)$$

$$r = (R_p + R_s)/2 \quad (2)$$

$$\Delta = \cos^{-1}(\pm -(2*R_{ph} - (R_p + R_s)/2)/(R_p * R_s)^{1/2})) \quad (3)$$

where $R_p$ is the output from photo detector 72p, $R_s$ is the output from photo detector 72s, and $R_{ph}$ is the output from photo detector 160.

Measurement of the total reflectivity r is possible with the optical measurement system of the present invention because photo detectors 72s and 72p measure the absolute reflectivity or intensity of the s- and p-polarization components. Because the incident illumination provided by prior art ellipsometers is typically less stable, prior art ellipsometers measure the ratio of the polarization components instead of the absolute reflectivity or intensity of the s- and p-polarization components and, thus, can not calculate the total reflectivity r. In contrast, the highly stabilized light source of the optical measurement system of the present invention permits direct measurement of the absolute reflectivity of the individual polarization components, and, thus, the determination of total reflectivity r.

In general applications, the light beam 110 is preferably directed at an angle approximately equal to Brewster's angle of the material present on the substrate surface. In situations in which multiple thin film layers overlay the substrate surface, for example in the case of a magnetic storage disk, the light beam 110 is preferably directed at an angle $\phi$ of about 60°, and generally between about 53° and roughly 70°, so that tan ($\phi$) lies between the index of refraction of the top thin film layer (e.g., the lubricant) and that of the bottom thin film layer (e.g., the carbon layer). By operating in a region where the light strikes above the Brewster's angle of one material (e.g., the lubricant) while being below the Brewster's angle for the other (the carbon layer) light of both polarizations will be represented in the collected light. Moreover, the relative amounts of detected s- and p-illumination, and the direction of change in intensity between two measurements can reveal the nature of changes in a simple logical array.

In general, the particular wavelength of the laser is not very important, since the lubricant film absorbs very little of the light at many available wavelengths, while the carbon film does absorb, but with a typical sensitivity which may be about 0.04% intensity change per Angstrom of film thickness. By stabilizing the output of the laser source as described above, applicant is able to repeatably detect such small changes in amplitude. The temperature stabilization not only enhances the intensity stability, but further assures that beam 110 remains relatively free of mode hopping, so that mode hops do not affect the intensity and wavelength; thus the $(r,\theta)$ coordinates taken at two different times will represent the same point P on the disk. The resolution of the reflectance map will in general depend on the spot size of the lens and the accuracy of the position monitoring means used to determine the location on the substrate.

The above apparatus has the advantage of being quantitatively accurate, and of having a "perfect memory" of substrate coordinates when the substrate remains on the turntable. In the example of the magnetic storage disk, typically about seventy per cent of the s-polarized light is reflected, while less than half of the p-polarized light is reflected. Operating against a substantially perfectly reflective background, the total variation of intensity of the reflected light beam due to effects such as scattering, carbon thickness, and texture variation and absorbance is only about two percent. However, with the aforesaid apparatus, variations of 0.1% are readily detected, and the reflectance range is readily expanded to enhance image contrast. The coordinate/intensity map has therefore been found to be quite useful. For example, a very high resolution map of lubricant thickness is obtained by mapping the surface, rinsing the lubricant off, and then compiling a second reflectance map and comparing the two maps pointwise. The CPU 200 may include software modules to determine a pointwise difference map, to expand the range of detected intensity changes and to print out a graphic image of the substrate. It may also include pattern detection software to detect and to annotate specific features.

Moreover, in certain applications a single measurement scan or cycle of the substrate will be a sufficient evaluation of the substrate surface. In such applications, determination of the location of each measurement point on the substrate surface is unnecessary and, thus, the position encoder or the like can be removed from the system. Such applications include, for example, measuring the flatness of the substrate surface or evaluating the uniformity of a thin film applied to the substrate surface.

The present system is useful in processes in which the film layer is deposited, etched, patterned, doped, oxidized, and annealed to evaluate changes in the thin film layer. For example, in sputtering processes in which a thin film layer is deposited onto a substrate, the optical measurement system of the present invention can be used to evaluate the optical characteristics as well as the thickness of the deposition layer to ensure uniform deposition thickness. The intensity of light measured by the detectors 72s, 72p, and 160 of the optical measurement system is sensitive to changes in the refractive index and absorption coefficient of the deposited film and the substrate, as well as changes in the thickness of the film. Other specific examples include evaluating insulation layer thickness (i.e., silicon dioxide thickness) on a silicon wafer during semiconductor device manufacturing processes and analyzing thin film coatings used in thin film display panels.

Alternatively, the three-dimensional topography of a substrate can be evaluated during processing. For example, the optical measurement system of the present invention can be used to evaluate changes in the optical characteristics of silicon and gallium arsenide wafers in semiconductor and microelectronic manufacturing processes to measure film thickness and uniformity of, for example, oxide, nitride, and photoresist films.

In addition, various enhanced measurement protocols may be implemented with the basic first embodiment discussed above.

Figure 2:
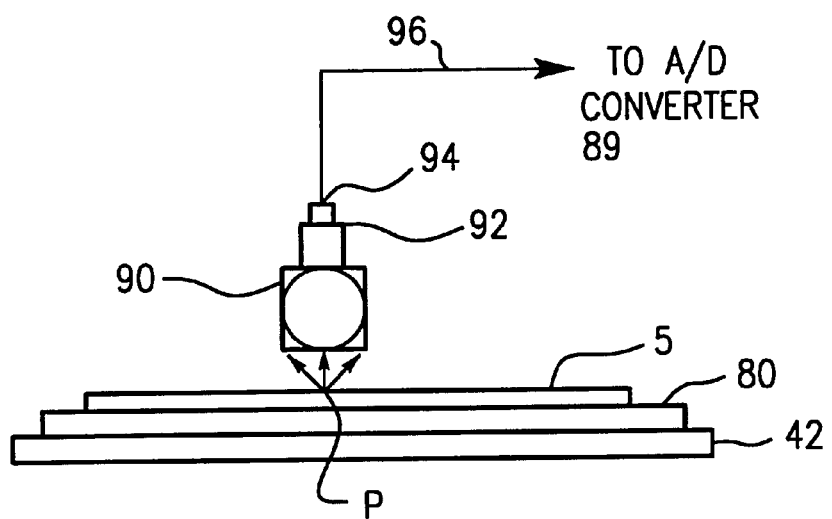
FIG. 2 is a schematic side view showing a system for measuring scattered light in accordance with the teachings of the present invention.

A second alternative embodiment of the optical measurement system of the present invention is shown in FIG. 2. In the second preferred embodiment, an integrating sphere 90 and filter 92 are provided above the substrate 5 to collect scattered light reflected from the substrate surface. The intensity of the scattered light is measured by photo-diode 94 and communicated to A/D converter 89 by line 96. The intensity of the scattered light measured by the integrating sphere 90 is sensitive to changes in substrate surface roughness and topography. Preferably, the integrating sphere 90 is positioned adjacent the substrate surface to maximize the amount of scattered light incident on the integrating sphere 90. In this position, light enters the integrating sphere 90 through the sides of the sphere. The integrating sphere 90 can alternatively be replaced with a diffuser.

Inclusion of the integrating sphere 90 allows the optical measurement system of the present invention to measure four parameters of the reflected light beam simultaneously in a single scan of the substrate: 1) the intensity of the s-polarized light component; 2) the intensity of the p-polarized (collectively, the s- and p-polarization reflectance); 3) the phase difference between the s- and p-polarization components; and 4) the intensity of scattered light.

Figure 3:
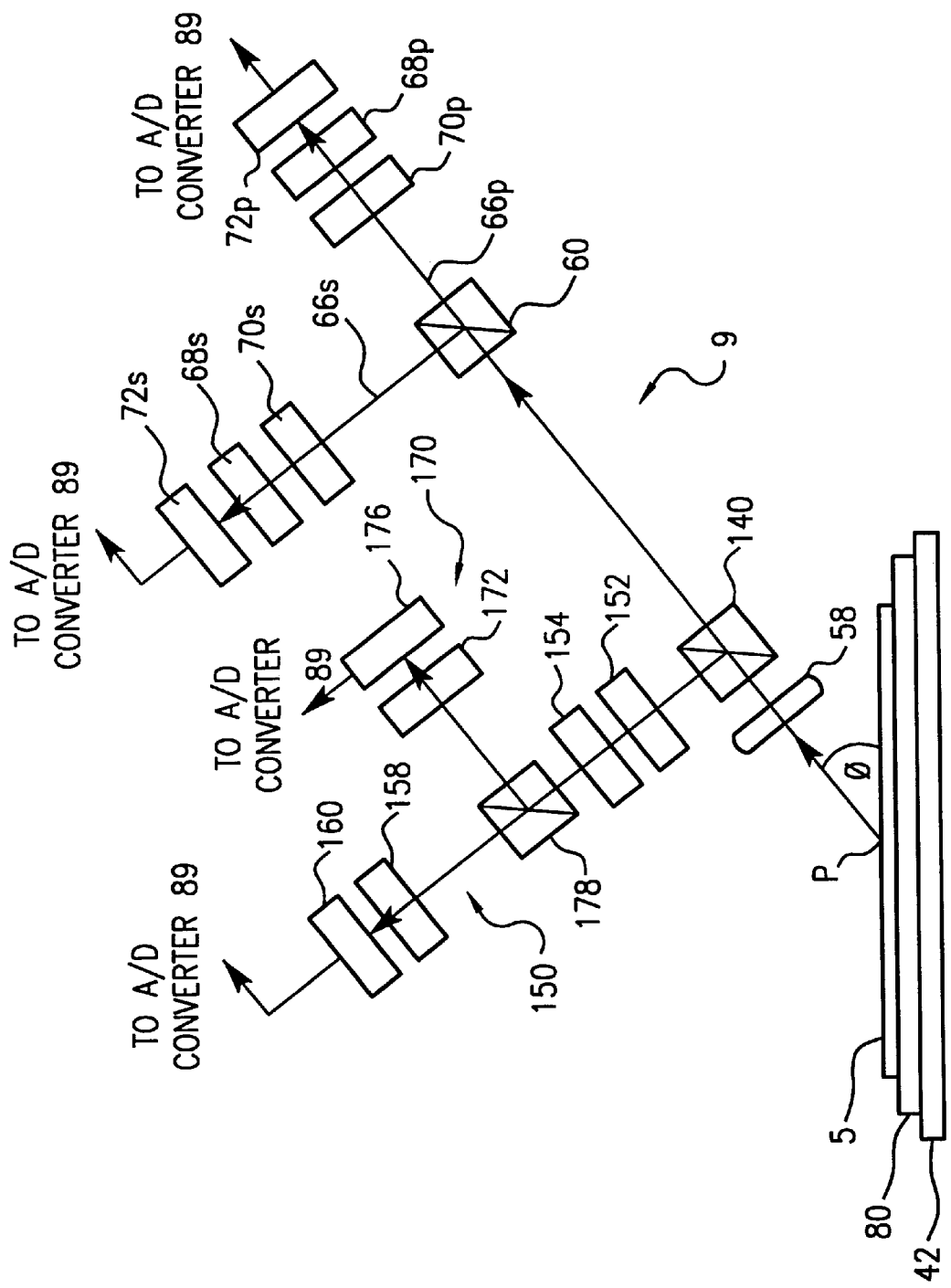
FIG. 3 is a schematic side view showing the detection system of an optical measurement system in accordance with an alternative embodiment of the present invention.

A third embodiment of the present invention is illustrated in FIG. 3, in which the detection system 9 of the present invention includes an additional detection subsystem 170 for determining the reflection angle of the reflected light beam during a measurement scan. The term "reflection angle" as used herein is inclusive of both the polar angle Ø, illustrated in FIG. 3, and the azimuthal angle θ (not shown). Measurement of the reflection angle provides a direct measurement of the long spatial wavelength roughness, such as waviness or flatness, of the sample under evaluation, as the reflection angle for each measurement point P is dependent on the angle of the substrate surface at the point P. Inclusion of the reflection angle detection subsystem 170 allows the optical measurement system of the present invention to measure four parameters of the reflected light beam simultaneously in a single scan of the substrate: 1) the intensity of the s-polarized light component; 2) the intensity of the p-polarized (collectively, the s- and p-polarization reflectance); 3) the phase difference between the s- and p-polarization components; and 4) the reflection angle. Moreover, by adding integrating sphere 90, as discussed above in connection with the description of the second embodiment, an additional fifth component, the intensity of scattered light, can also be simultaneously measured.

The reflection angle detection subsystem 170 includes a quadrant photo detector 176, available from UDT Sensors, Inc. of Hawthorne, Calif., as well as, a band pass filter 172. The linear polarizing element 156 of the phase detection subsystem 150 can be replaced with a polarizing beam splitting cube 178 which produces two beams, one received by photo detector 160 and the other received by quadrant photo detector 176. In the alternative, a separate non-polarizing beam splitter (not shown) can be provided in the optic path between beam splitter 140 and the photo detector 160 to direct a portion of the reflected light to the quadrant photo detector 176.

It is to be understood that the present invention is not limited to the embodiments described above, but encompasses any and all embodiments within the scope of the following claims.

We claim:

1. An optical measurement system for evaluating a substrate, the system comprising:
   an intensity stabilized light source configured to generate a stabilized light beam,
   a polarizing element for polarizing the light beam emanating from the light source to provide a polarized light beam,
   an optical system for directing the polarized light beam to a particular location on the substrate,
   a controllable translatable assembly for moving the polarized light beam across at least a portion of the substrate such that the polarized light beam impinges upon multiple locations on the substrate,
   a position indicating means for determining the particular location on the substrate upon which the polarized light beam impinges,
   a detection system configured to evaluate light reflected from the particular locations on the substrate upon which the polarized light beam impinges, the detection system including
      a polarization analyzing element for separating the light from the particular locations on the substrate into s-polarized light and p-polarized light,
      a first optical sensor measuring amplitude of the s-polarized light,
      a second optical sensor measuring amplitude of the p-polarized light, and
      a third optical sensor measuring reflection angle of the reflected light relative to the substrate, and
   a control system for compiling a data set correlating the measured amplitude of the s-polarized light, the p-polarized light, and the measured reflection angle with the particular location on the substrate upon which the polarized light beam impinges for determining changes in the substrate.

2. The optical measurement system of claim 1, wherein a light source feedback system controls and stabilizes the intensity of the light beam.

3. The optical measurement system of claim 2, wherein the light source feedback system includes
   a photo-diode for measuring the intensity of the light beam and generating an output signal based on the measured intensity, and
   a light source controller coupled to the light source and the photo-diode, the light source controller controlling and stabilizing the light beam based on the output signal received from the photo-diode.

4. The optical measurement system of claim 1, further comprising a non-polarizing beam splitter for directing a portion of the light beam to the photo-diode.

5. The optical measurement system of claim 1, further comprising a system for measuring scattered light reflected from the substrate.

6. The optical measurement system of claim, 5, wherein the system for collecting and measuring scattered light includes an integrating sphere.

7. The optical measurement system of claim 1, wherein the detection system further includes a non-polarizing beam splitter directing a portion of the reflected light beam to the third optical sensor.

8. The optical measurement system of claim 1, wherein the third optical sensor is a quadrant photo-detector.

9. The optical measurement system of claim 1, wherein the detection system further includes a fourth optical sensor measuring phase difference between the s-polarized light and the p-polarized light.

10. The optical measurement system of claim 1, wherein the polarization analyzing element is a polarizing beamsplitter.

11. The optical measurement of claim 1, further comprising a light source monitoring system for monitoring the intensity of the light beam.

12. A method of evaluating a substrate comprising the steps of generating an intensity stabilized light beam;

polarizing the light beam to form a polarized light beam, directing the polarized light beam to a particular location on the substrate, separating the polarized light beam after reflection from the particular location on the substrate into two orthogonally polarized light beams, measuring the amplitude of each of the orthogonally polarized light beams, measuring the reflection angle of the reflected light relative to the substrate, and analyzing the measured amplitude of each of the two orthogonally polarized light beams and the measured reflection angle of reflected light beam to determine changes in the substrate.

13. The method of claim 12, further comprising the steps of monitoring the intensity of the light beam, and controlling and stabilizing the intensity of the light beam based on the monitored light intensity.

14. The method of claim 12, further comprising the step of measuring scattered light reflected from the substrate and wherein the step of analyzing includes analyzing the measured scattered light to determine changes in the substrate.

15. The method of claim 12, further comprising the step of measuring the phase difference between the two orthogonally polarized light beams and wherein the step of analyzing includes analyzing the measured phase difference to determine changes in the substrate.

* * * * *